(12) United States Patent
Briscoe et al.

(10) Patent No.: US 8,146,448 B2
(45) Date of Patent: Apr. 3, 2012

(54) APPARATUS FOR MOBILE COLLECTION OF ATMOSPHERIC SAMPLE FOR CHEMICAL ANALYSIS

(75) Inventors: Matthew Briscoe, Zionsville, IN (US); Brent Rardin, Lafayette, IN (US); Dennis Barket, Jr., Lafayette, IN (US)

(73) Assignee: Griffin Analytical Technologies, LLC, West Lafayette, IN (US)

( * ) Notice: Subject to any disclaimer, the term of this patent is extended or adjusted under 35 U.S.C. 154(b) by 730 days.

(21) Appl. No.: 12/216,027

(22) Filed: Jun. 27, 2008

(65) Prior Publication Data

US 2009/0000404 A1 Jan. 1, 2009

Related U.S. Application Data

(60) Provisional application No. 60/929,506, filed on Jun. 29, 2007.

(51) Int. Cl.
*G01N 1/22* (2006.01)
*G01N 1/24* (2006.01)
*G01N 1/40* (2006.01)

(52) U.S. Cl. ............... 73/864.91; 73/863.23; 73/863.52; 73/863.57; 73/864.63

(58) Field of Classification Search ............... 73/863.21, 73/863.23, 863.25, 863.52, 863.57, 863.71, 73/864.34, 864.51–864.52, 864.63, 864.91
See application file for complete search history.

(56) References Cited

U.S. PATENT DOCUMENTS

| | | | |
|---|---|---|---|
| 3,241,371 A * | 3/1966 | Horeth | ...................... 73/863.23 |
| 4,091,674 A | 5/1978 | Amey | |
| 4,170,901 A | 10/1979 | Conkle et al. | |
| 4,546,659 A | 10/1985 | Gill et al. | |
| 4,584,887 A | 4/1986 | Galen | |
| 4,718,268 A | 1/1988 | Reid et al. | |
| 4,760,881 A * | 8/1988 | Long et al. | ............. 73/863.21 X |
| 5,124,274 A | 6/1992 | Ohki et al. | |
| 5,138,889 A | 8/1992 | Conrad | |
| 5,142,143 A | 8/1992 | Fite et al. | |
| 5,288,310 A | 2/1994 | Peters et al. | |
| 5,402,668 A | 4/1995 | Murakami et al. | |
| 5,437,199 A * | 8/1995 | Kaplan | ...................... 73/863.23 |

(Continued)

FOREIGN PATENT DOCUMENTS

GB 2056304 A * 3/1981

(Continued)

OTHER PUBLICATIONS

V. Camel et al., Trace enrichment methods for the determination of organic pollutants in ambient air, Journal of Chromatography A, vol. 710, No. 1, pp. 3-19 (1995).

(Continued)

*Primary Examiner* — Thomas P Noland
(74) *Attorney, Agent, or Firm* — Wells St. John P.S.

(57) ABSTRACT

Portable devices and related methods for collecting and storing atmospheric samples for subsequent chemical analysis are provided. A sample cartridge according to one implementation includes self-sealing inlet and outlet ports configured to close automatically when not in use, and a sample retention portion between the inlet and outlet ports that is adapted to trap an atmospheric sample. The sample cartridge may also include a memory device for recording data regarding the sample. Another embodiment provides a portable sampler configured to removably secure a self-sealing sample cartridge. A portable sampling device may also be used with an analytical instrument. The analytical instrument may analyze the sample and read the data recorded on the sample cartridge's memory.

24 Claims, 21 Drawing Sheets

U.S. PATENT DOCUMENTS

| | | | |
|---|---|---|---|
| 5,500,369 A | | 3/1996 | Kiplinger |
| 5,551,278 A | | 9/1996 | Rounbehler et al. |
| 5,585,575 A | * | 12/1996 | Corrigan et al. ............ 73/863.71 |
| 5,597,535 A | * | 1/1997 | Schaedlich et al. ............. 422/88 |
| 5,826,577 A | | 10/1998 | Perroz, Jr. et al. |
| 6,167,767 B1 | | 1/2001 | Mengel et al. |
| 6,230,573 B1 | | 5/2001 | Schulten et al. |
| 6,321,609 B1 | | 11/2001 | Mengel et al. |
| 6,339,965 B1 | * | 1/2002 | Pasquereau et al. ... 73/863.21 X |
| 6,446,514 B1 | | 9/2002 | Danylewych-May et al. |
| 6,450,784 B2 | * | 9/2002 | Newcomer .................... 417/394 |
| 6,477,905 B1 | | 11/2002 | Mitra |
| 6,477,906 B1 | | 11/2002 | Peterson |
| 6,723,056 B1 | | 4/2004 | Alving et al. |
| 6,819,253 B2 | | 11/2004 | Albro et al. |
| 6,989,130 B2 | * | 1/2006 | Deshmukh ...................... 422/81 |
| 7,161,142 B1 | | 1/2007 | Patterson et al. |
| 7,171,312 B2 | | 1/2007 | Steinthal et al. |
| 7,227,472 B1 | * | 6/2007 | Roe ............................... 340/576 |
| 7,600,439 B1 | * | 10/2009 | Patterson et al. .......... 73/863.21 |
| 7,874,221 B1 | * | 1/2011 | Mayeaux ............... 73/863.71 X |
| 7,875,109 B1 | * | 1/2011 | Mayeaux ............... 73/864.91 X |
| 7,921,739 B2 | * | 4/2011 | Fjerdingstad et al. ..... 73/863.71 |
| 2004/0123679 A1 | | 7/2004 | Coleman et al. |
| 2004/0224422 A1 | | 11/2004 | Bonne et al. |
| 2008/0229805 A1 | | 9/2008 | Barket et al. |

FOREIGN PATENT DOCUMENTS

| | | |
|---|---|---|
| RU | 2006021 C1 * | 1/1994 |
| WO | WO-00/26405 | 5/2000 |
| WO | WO-02/40964 A1 | 5/2002 |
| WO | WO 2005/047865 | 5/2005 |
| WO | WO 2005/103641 | 11/2005 |
| WO | WO-2006/062906 | 6/2006 |

OTHER PUBLICATIONS

Markes International Ltd., Chemical Warfare Agents & Homeland Security (2008), http://www.markes.com/en/ChemicalWarfare/default.aspx (last visited Mar. 11, 2008), pp. 1-2.
Teledyne Technologies, Inc., Teledyne Tekmar Products (2006), http://www.teledynetekmar.com/products/index.asp (last visited Mar. 11, 2008), 1 page.
CDS Analytical, Inc., Dynatherm Chemical Agent Monitors Home Page (2004), http://www.cdsanalytical.com/dynatherm/dynatherm.html (last visited Mar. 11, 2008), pp. 1-2.
Inficon, Inficon Product Index, http://www.inficon.com/en/productindex.html (last visited Mar. 12, 2008), pp. 1-4.
Inficon, HAPSITE Chemical Identification System Brochure (2004), available at http://www.inficon.com/download/en/HAPSchemidentsys.pdf (last visited Mar. 12, 2008), 4 pages.
Inficon, HAPSITE Headspace Sampling System Brochure (2003), available at http://www.inficonchemicalidentificationsystems.com/en/pdf/HAPSITEheadspace.pdf (last visited Mar. 11, 2008), 2 pages.
Inficon, HAPSITE Accessory Catalog (2007), available at http://www.inficon.com/download/en/dild30a1%20/020HAPSITE%20Accessory%20Catalog.pdf (last visited Mar. 11, 2008), 66 pages.
Inficon, HAPSITE Situprobe Brochure (2007), available at http://www.inficon.com/download/en/situprobe.pdf (last visited Mar. 11, 2008), 2 pages.
Inficon, HAPSITE Smart Chemical Identification System Brochure (2004), available at http://www.inficon.com/download/en/haps-smart.pdf (last visited Mar. 11, 2008), 2 pages.
Inficon, HAPSITE Smart Plus Chemical Identification System Brochure (2007), available at http://www.inficon.com/download/en/HAPSITE_Smart_Plus_LR.pdf (last visited Mar. 11, 2008), 2 pages.
Inficon, HAPSITE VIPER Chemical Identification System with 267 Surface Sampler Brochure (2006), available at http://www.inficon.com/download/en/hapsitev.pdf (last visited Mar. 11, 2008), 2 pages.
Inficon, Scentograph CMS100 Brochure (2003), available at http://www.inficonchemicalmonitoringsystems.com/en/Scentographcms100.html (last visited Mar. 11, 2008), 2 pages.
Inficon, Scentograph CMS200 Brochure (2003), available at http://www.inficonchemicalmonitoringsystems.com/en/pdf/Scentograph_CMS200_Brochure.pdf (last visited Mar. 11, 2008), 2 pages.
Hi-Q Environmental Products Co., HVP-3800AFC & HVP-3500AFC Series Samplers Information Page, available at http://store.hi-q.net/Item/Page3.htm (last visited Mar. 11, 2008), pp. 1-2.
Hi-Q Environmental Products Co., HVP-4200AFC & HVP-4300AFC Series Information Page, available at http://store.hi-q.net/Item/HVP4200AFCHVP4300AFCSeries.htm (last visited Mar. 11, 2008), pp. 1-2.
Spectrex Corp., Operating Manual PAS-2000 Personal Air Sampler, available at http://www.spectrex.com/html_files/pdf/PAS-2000%20manual.pdf (last visited Mar. 11, 2008), Jan. 2006, 9 pages.
Spectrex Corp., Operating Manual PAS-500 Personal Air Sampler, available at http://www.spectrex.com/html_files/pdf/PAS500manual.pdf (last visited Mar. 11, 2008), 2 pages.
International Search Report for Application No. GB0811814.3 dated as searched on Oct. 21, 2008 (2 pages).

* cited by examiner

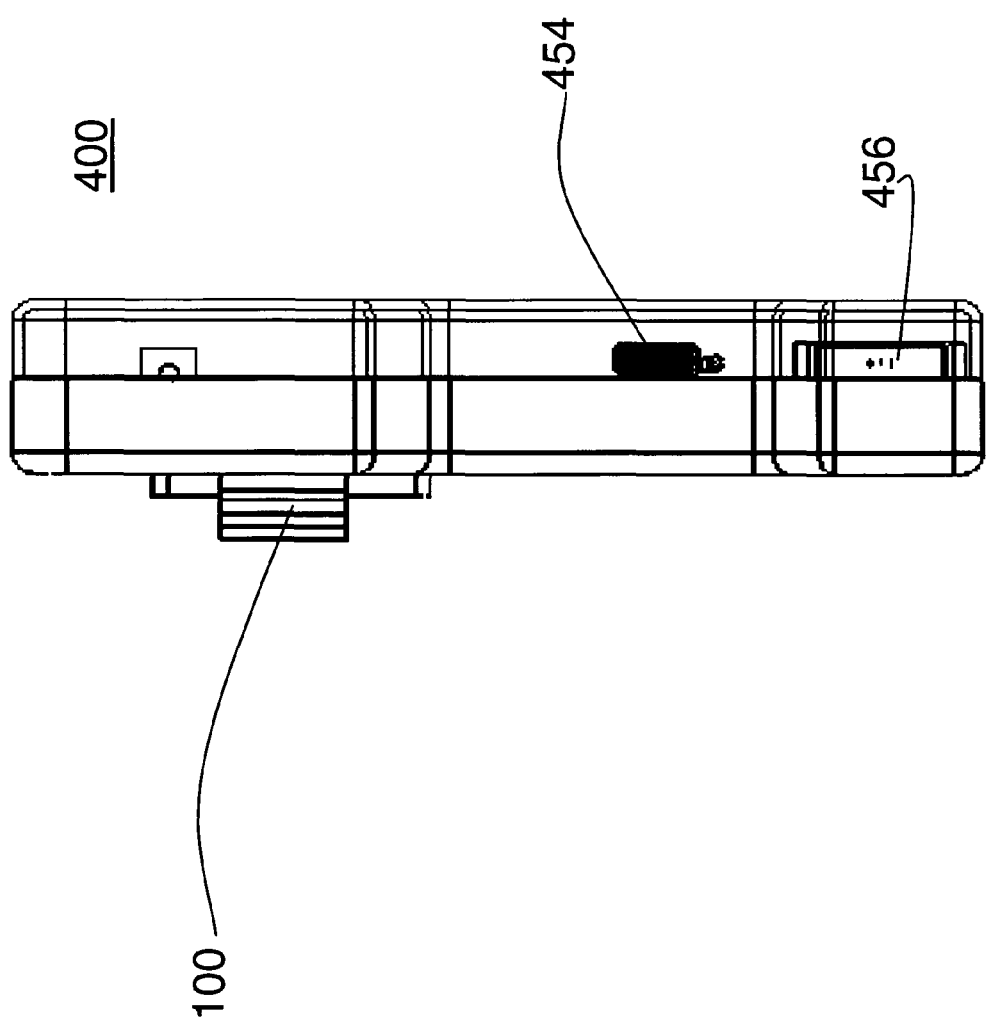

APPARATUS FOR MOBILE COLLECTION OF ATMOSPHERIC SAMPLE FOR CHEMICAL ANALYSIS

CROSS-REFERENCE TO RELATED APPLICATION

This application claims the benefit of U.S. Provisional Application No. 60/929,506, filed Jun. 29, 2007, by Matthew D. Briscoe, Brent Rardin, and Dennis J. Barket, Jr. and titled APPARATUS FOR MOBILE COLLECTION OF ATMOSPHERIC SAMPLE FOR CHEMICAL ANALYSIS, the disclosure of which is expressly incorporated herein by reference.

FIELD

The present disclosure relates to hand-held or portable devices and related methods for collecting and storing atmospheric samples for subsequent chemical analysis.

BACKGROUND

Recently, there has been an increased demand for portable devices to collect atmospheric samples for chemical analysis. Currently, several types of portable samplers exist, such as that disclosed in PCT Publication No. WO/2006/062906, which is hereby incorporated by reference. Other examples of portable samplers may be found at U.S. Pat. No 7,171,312 and U.S. Pat. No. 6,321,609.

Often these samplers suffer from a variety of drawbacks. For example, in many applications, the sampler must be decontaminated after sample collection but before analysis of the sample. In current applications, however, it is often difficult to decontaminate the sampler without affecting the sample since introduction of common decontamination cleaning agents into the sampler can destroy the collected sample. In addition, often the location where the sample is stored in the sampler is subject to contamination from other sources if not properly sealed. Further, the samplers often have no ability to store information regarding the sample or environmental conditions in the sampling environment. Thus, the operator must separately record this information. In some instances, this information is either not properly recorded or is not properly correlated to the correct sample.

It is accordingly an object of the disclosure to address these issues with handheld samplers.

SUMMARY

Apparatus consistent with one embodiment provide a sample cartridge for storing an atmospheric sample. The sample cartridge comprises a self-sealing inlet port configured to automatically close when the inlet port is not in use; a self-sealing outlet port configured to automatically close when the outlet port is not in use; and a sample retention portion in fluid communication with and disposed between the inlet port and outlet port and adapted to trap an atmospheric sample.

Apparatus consistent with another embodiment provide a portable sampler for collecting a sample. The portable sampler includes a portable housing having an interior portion. The portable housing is configured to removably secure a sample cartridge within the interior portion, the sample cartridge having a self-sealing inlet port and a self-sealing outlet port. The portable housing is further configured to open the self-sealing inlet port and the self-sealing outlet port when the sample is secured therein. A portable sampler also includes a sample inlet in communication with an area outside the housing and configured to establish fluid communication with the sample cartridge when the sample cartridge is secured; a pump configured to draw a sample into the sample cartridge through the sample inlet when the sample cartridge is secured; a processor configured to operate the sampler; and an input/output interface.

A system consistent with another embodiment provides a sampler, an analytical instrument, and a sample cartridge configured to be removably inserted within the sampler. The sample cartridge includes a first port including a first valve configured to self-close when the sample cartridge is not inserted within the sampler; a second port including a second valve configured to self-close when the sample cartridge is not inserted within the sampler; and a sample trap in fluid communication with the first port and the second port.

An additional embodiment provides a method of collecting and analyzing a sample. The method includes providing a sample cartridge, the sample cartridge comprising a self-sealing inlet port configured to automatically close when the inlet port is not in use; a self-sealing outlet port configured to automatically close when the outlet port is not in use; and a sample trap in fluid communication with and disposed between the inlet port and outlet port and adapted to trap a sample. The method also includes providing a sampler having a sampler inlet and an interior portion, the interior portion being configured to releasably receive the sample cartridge; inserting the sample cartridge into the sampler, whereby at least one of the self-sealing inlet port and self-sealing outlet port is opened; and, collecting a sample through the sampler inlet and into the sample trap.

Additional objects and advantages will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments and together with the description, serve to explain the principles of the disclosure. Additionally, it is contemplated that individual features of one embodiment may be added to, or substituted for, individual features of another embodiment. Accordingly, it is within the scope of this disclosure to cover embodiments resulting from substitution and replacement of different features between different embodiments.

BRIEF DESCRIPTION OF THE DRAWINGS

FIG. 4B is a side view of a handheld sampler with a cartridge installed in accordance with another embodiment;

DESCRIPTION OF THE EMBODIMENTS

Reference will now be made in detail to the present exemplary embodiments, examples of which are illustrated in the accompanying drawings.

One embodiment entails a hand-held or otherwise portable sampler 300 for collecting and storing atmospheric samples for subsequent analysis, such as, e.g., chemical analysis. The atmospheric samples collected by the sampler 300 may include a matrix, such as, e.g., atmospheric gasses like oxygen and nitrogen, that contain materials to be analyzed, including potentially harmful chemical contaminants or pollutants, biological materials such as, e.g., anthrax spores, and radioisotopes to be subsequently analyzed. Hereinafter, the materials collected by the sampler 300 will be referred to as analytes.

Figure 1A:
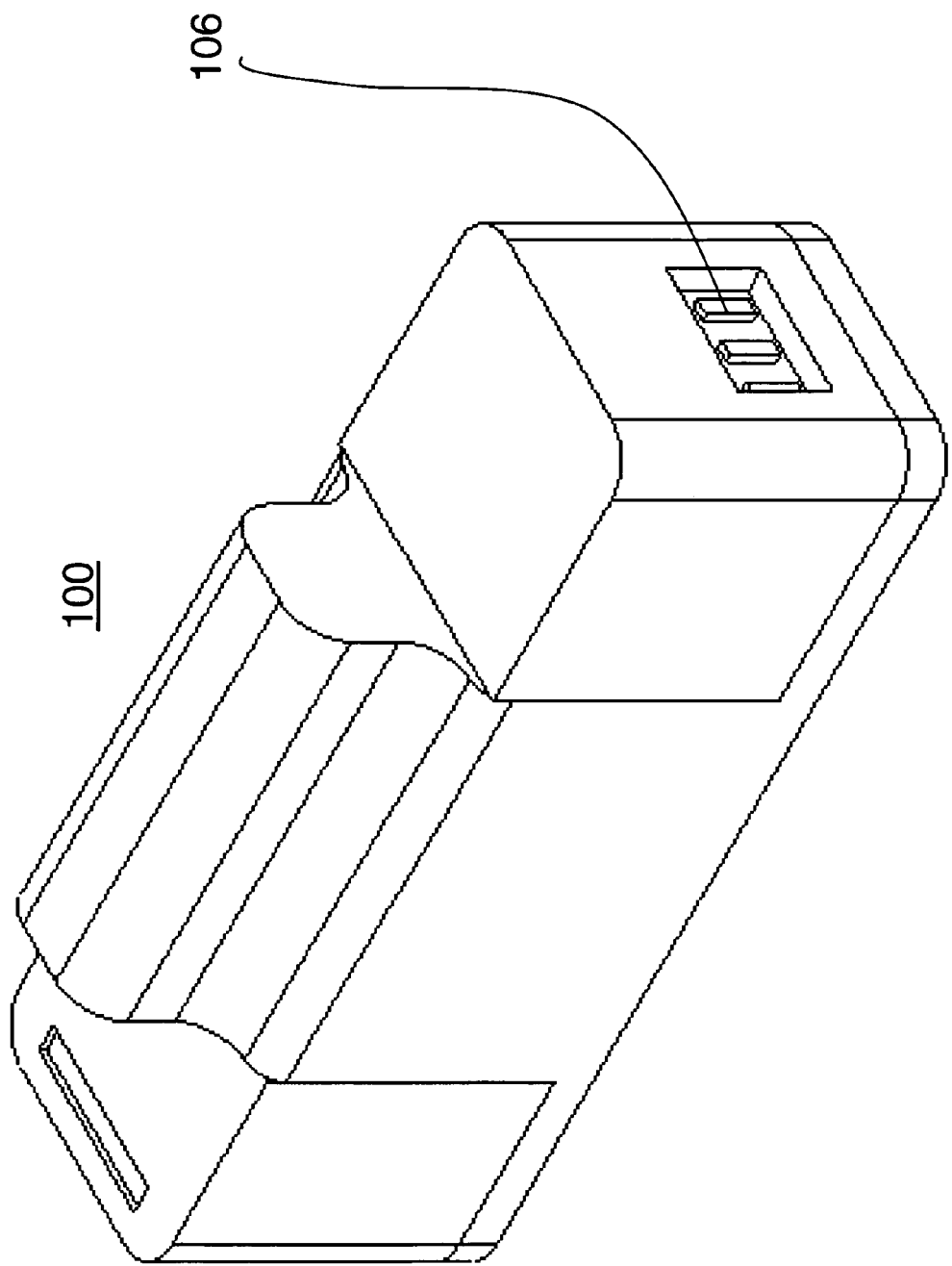
FIG. 1A is a perspective view of a cartridge for a handheld sampler in accordance with one embodiment.
Figure 1B:
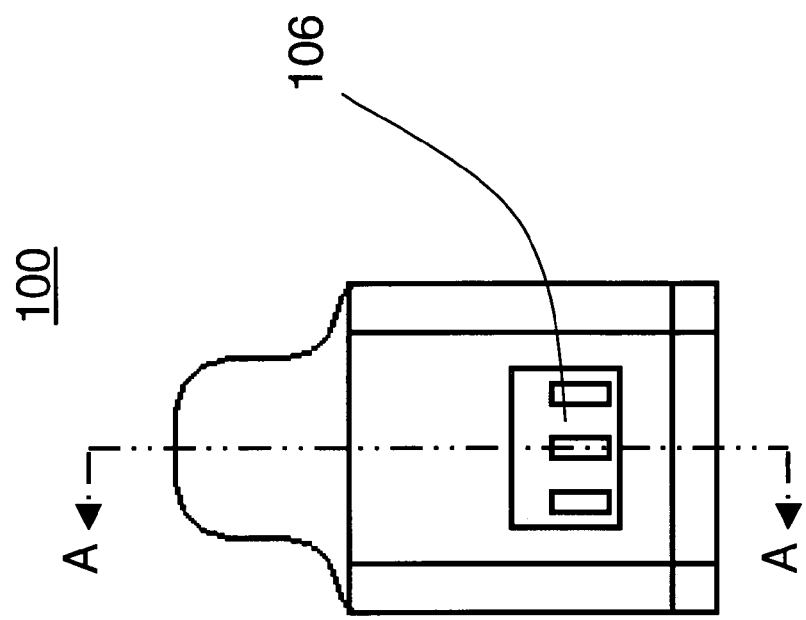
FIG. 1B is a front view of a cartridge for a handheld sampler in accordance with one embodiment.
Figure 1C:
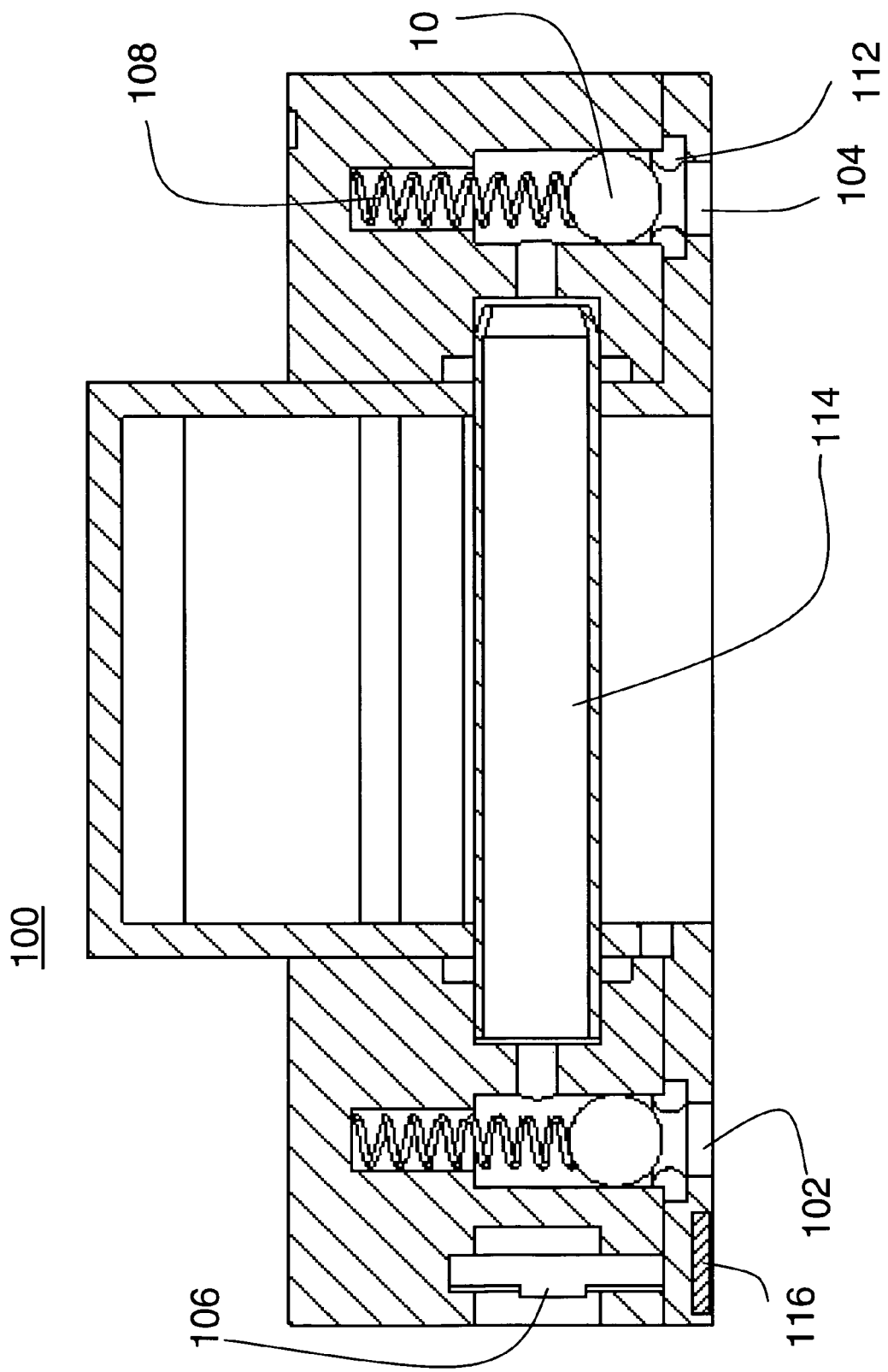
FIG. 1C is a side cross-section view of a cartridge for a handheld sampler along line A-A of FIG. 1B in accordance with one embodiment.
Figure 2A:
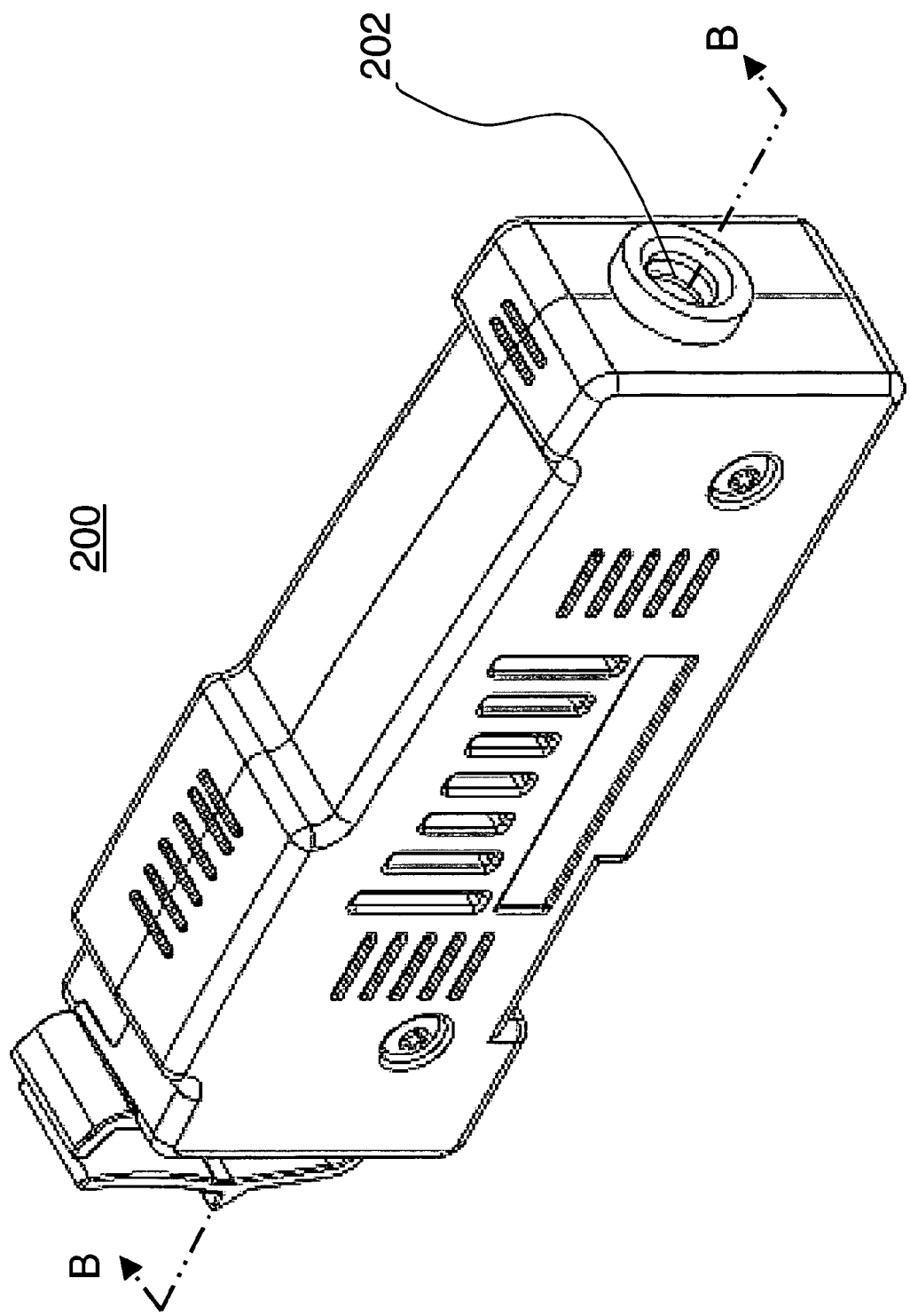
FIG. 2A is a perspective view of a cartridge for a handheld sampler in accordance with an additional embodiment.
Figure 2B:
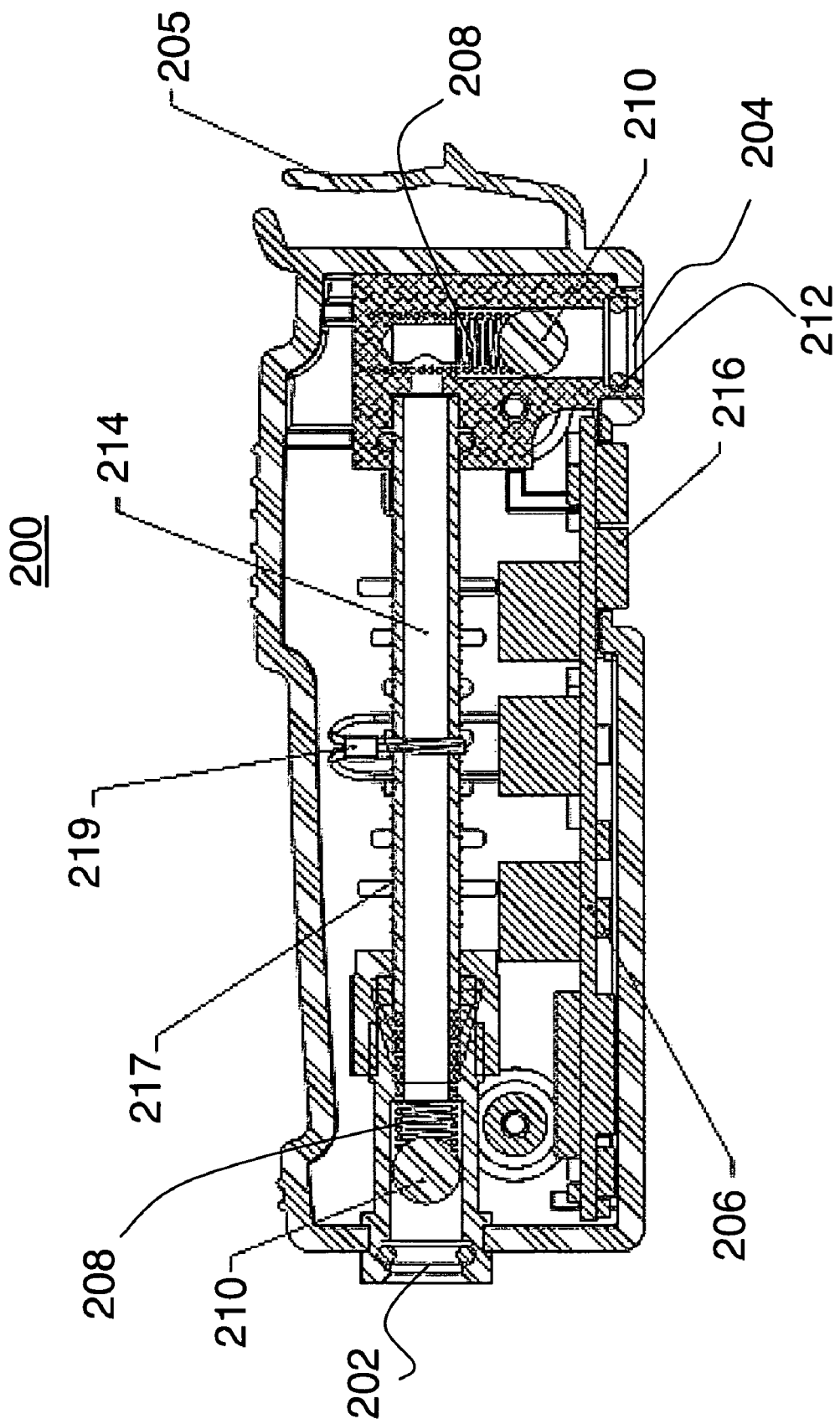
FIG. 2B is a side cross-section view of a cartridge for a handheld sampler along line B-B of FIG. 1D in accordance with an additional embodiment.
Figure 4A:
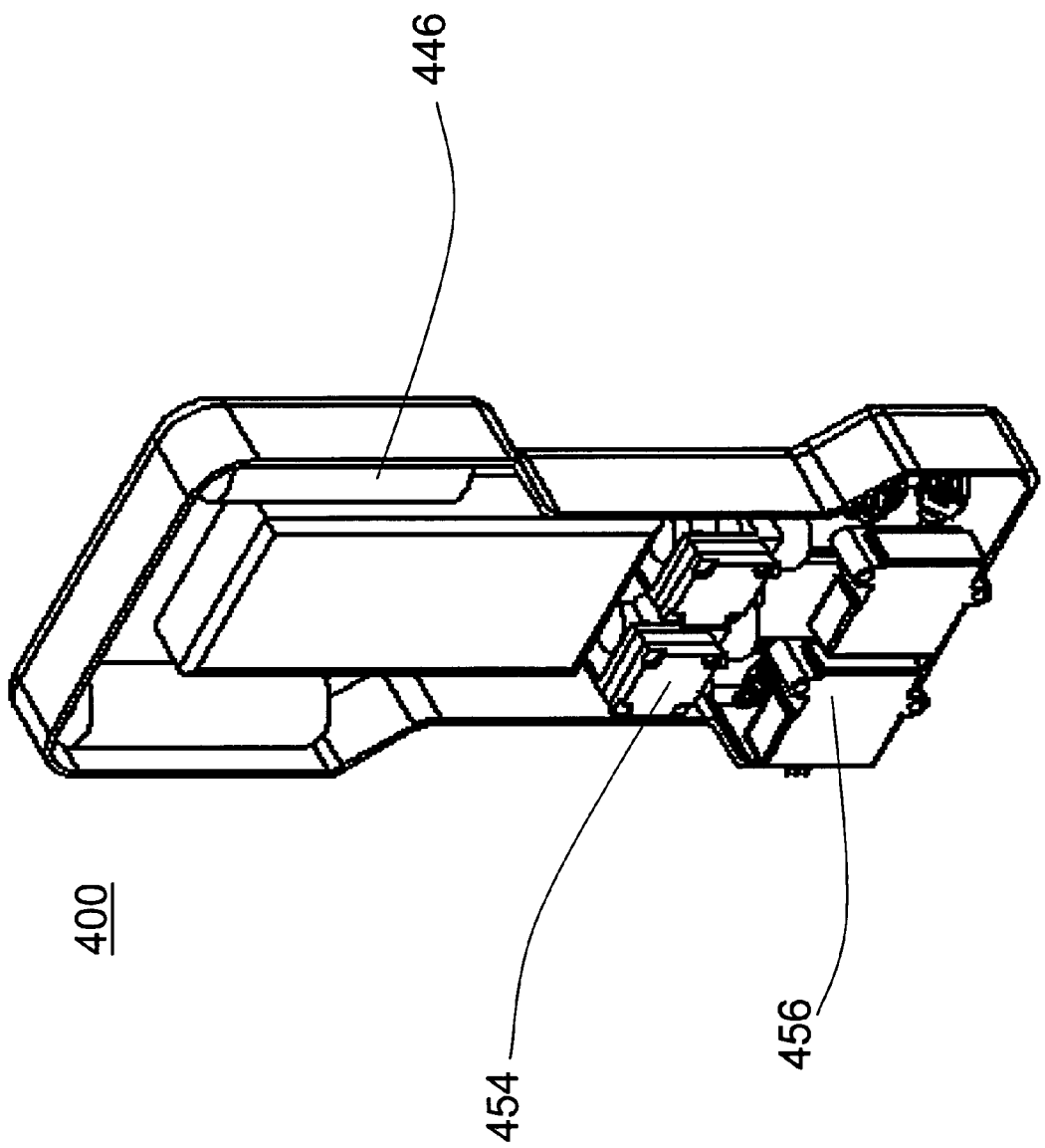
FIG. 4A is a perspective view of a handheld sampler with a cartridge installed in accordance with another embodiment.
Figure 4C:
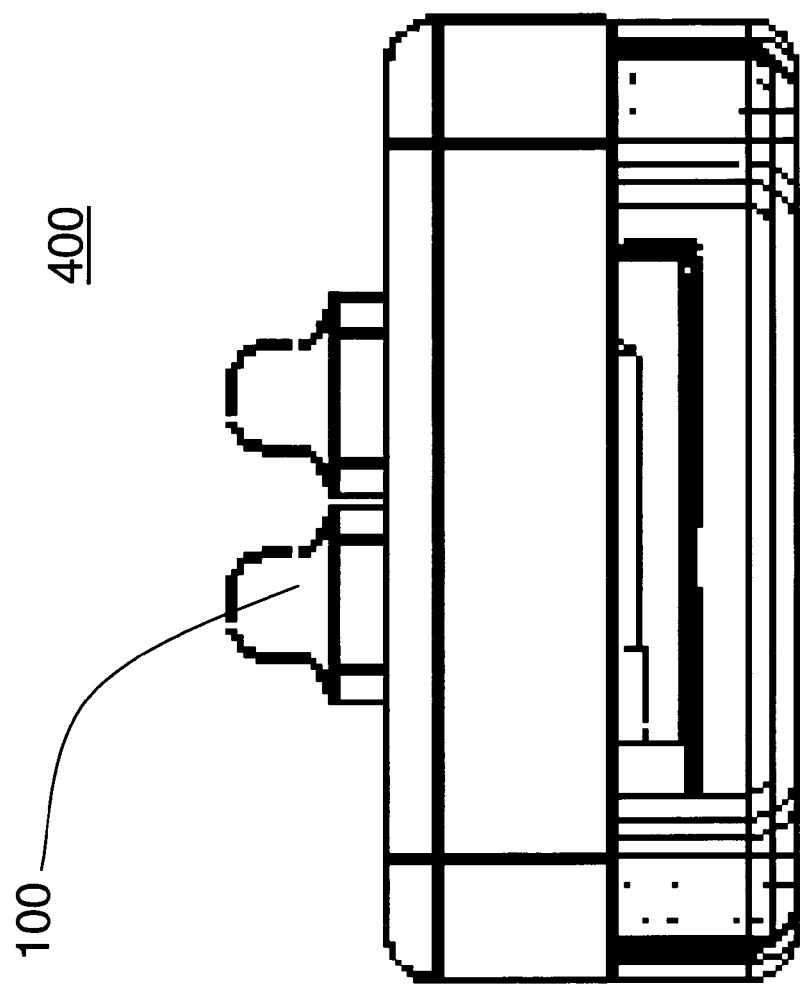
FIG. 4C is a top view of a handheld sampler with a cartridge installed in accordance with another embodiment.
Figure 4D:
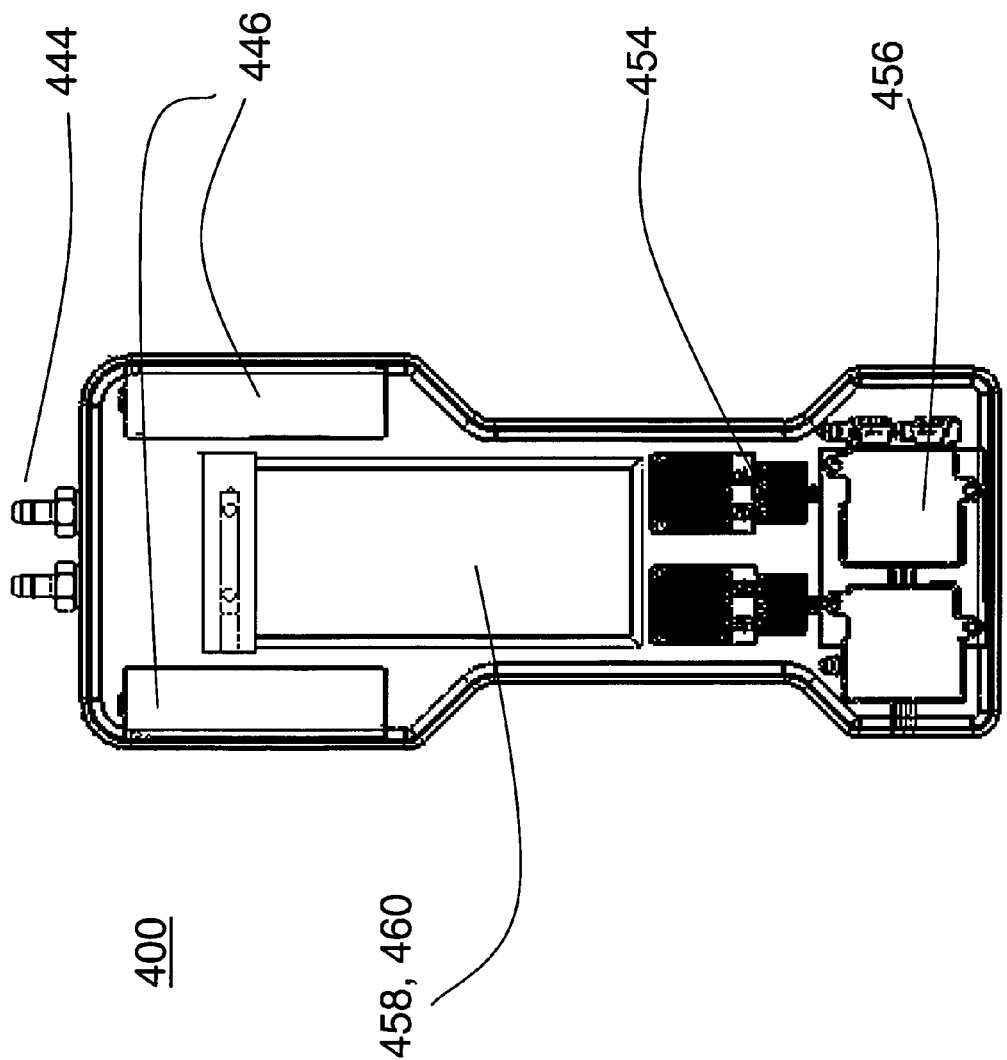
FIG. 4D is a front view of a handheld sampler with a cartridge installed in accordance with another embodiment.
Figure 5A:
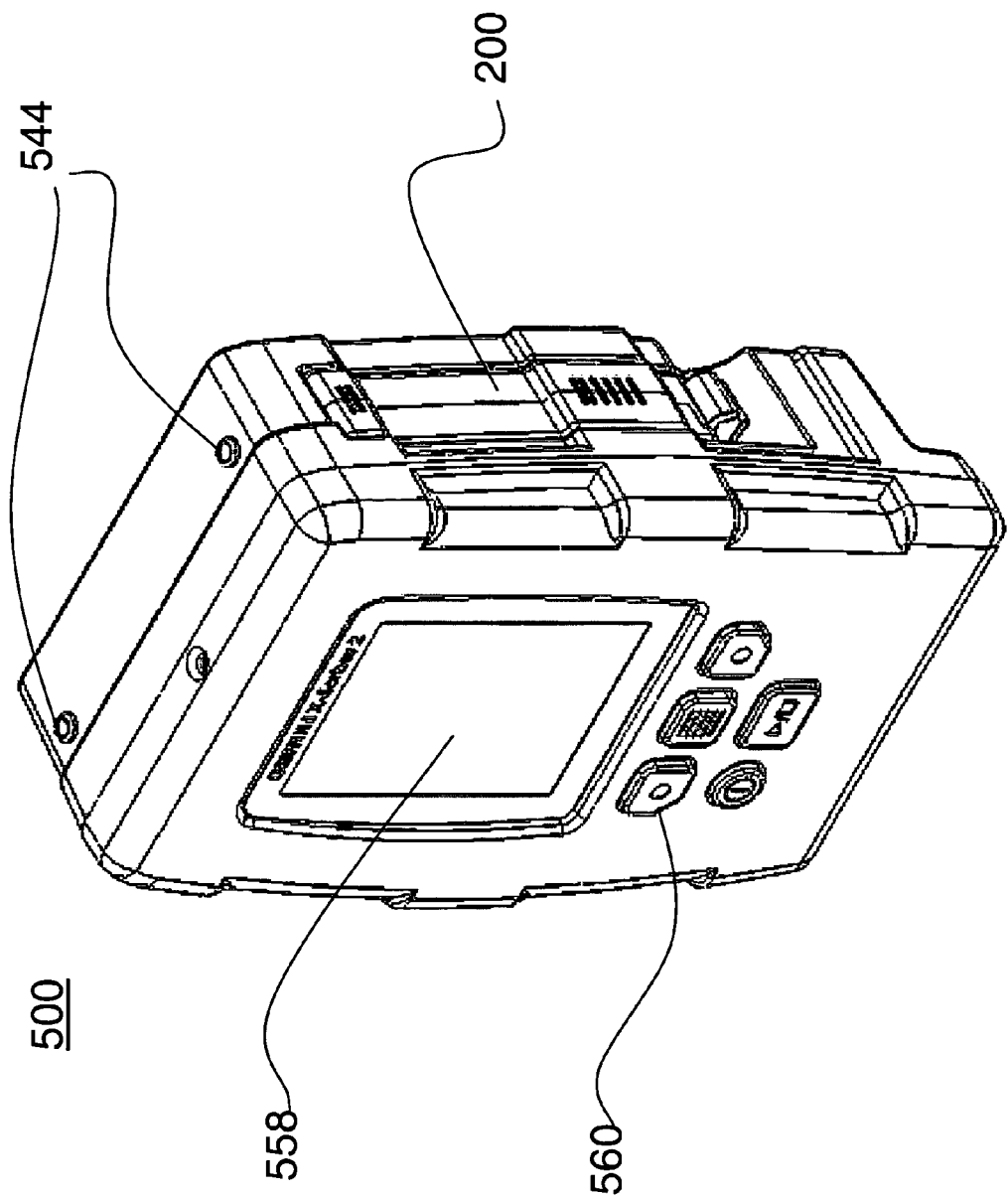
FIG. 5A is a perspective view of a handheld sampler with a cartridge installed in accordance with an additional embodiment.
Figure 5B:
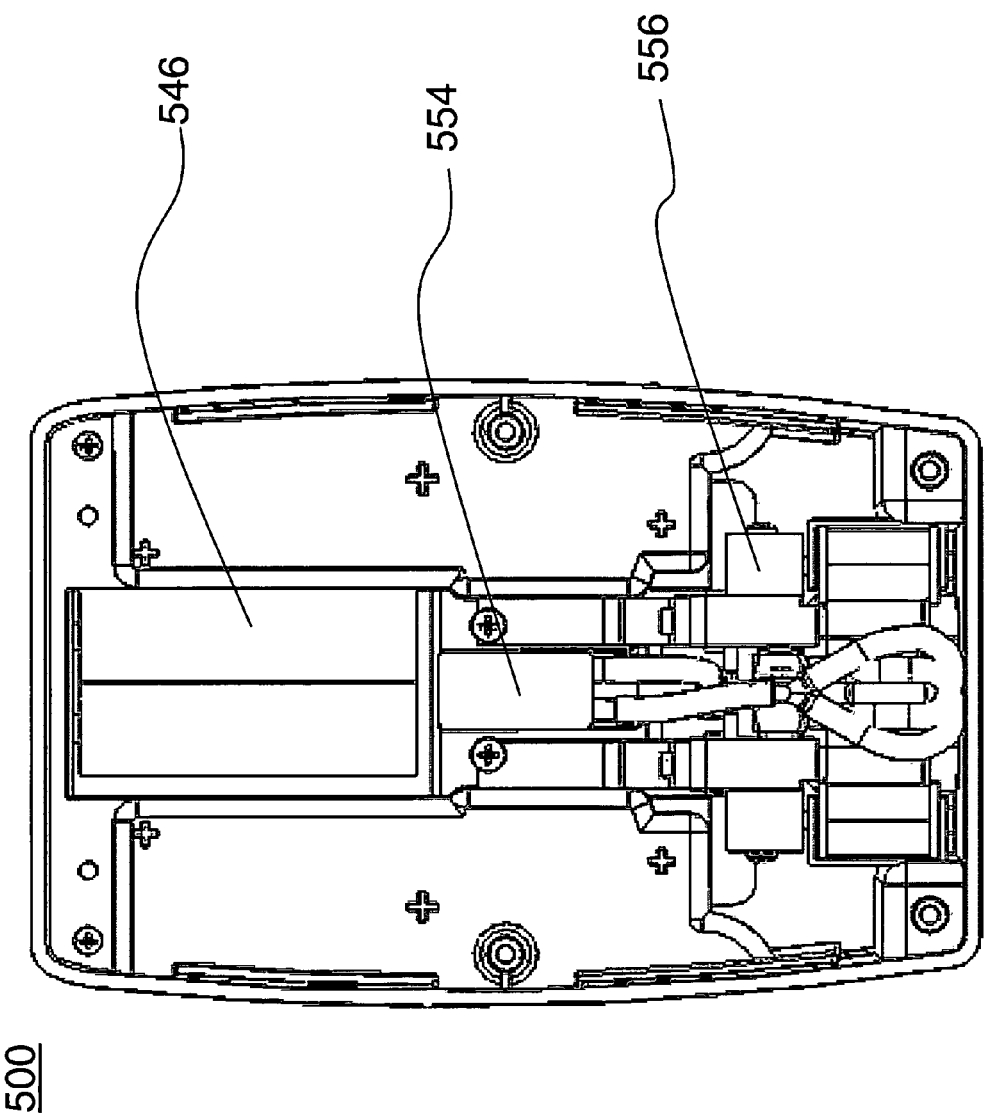
FIG. 5B is a front cross-section of a handheld sampler in accordance with an additional embodiment.
Figure 6:
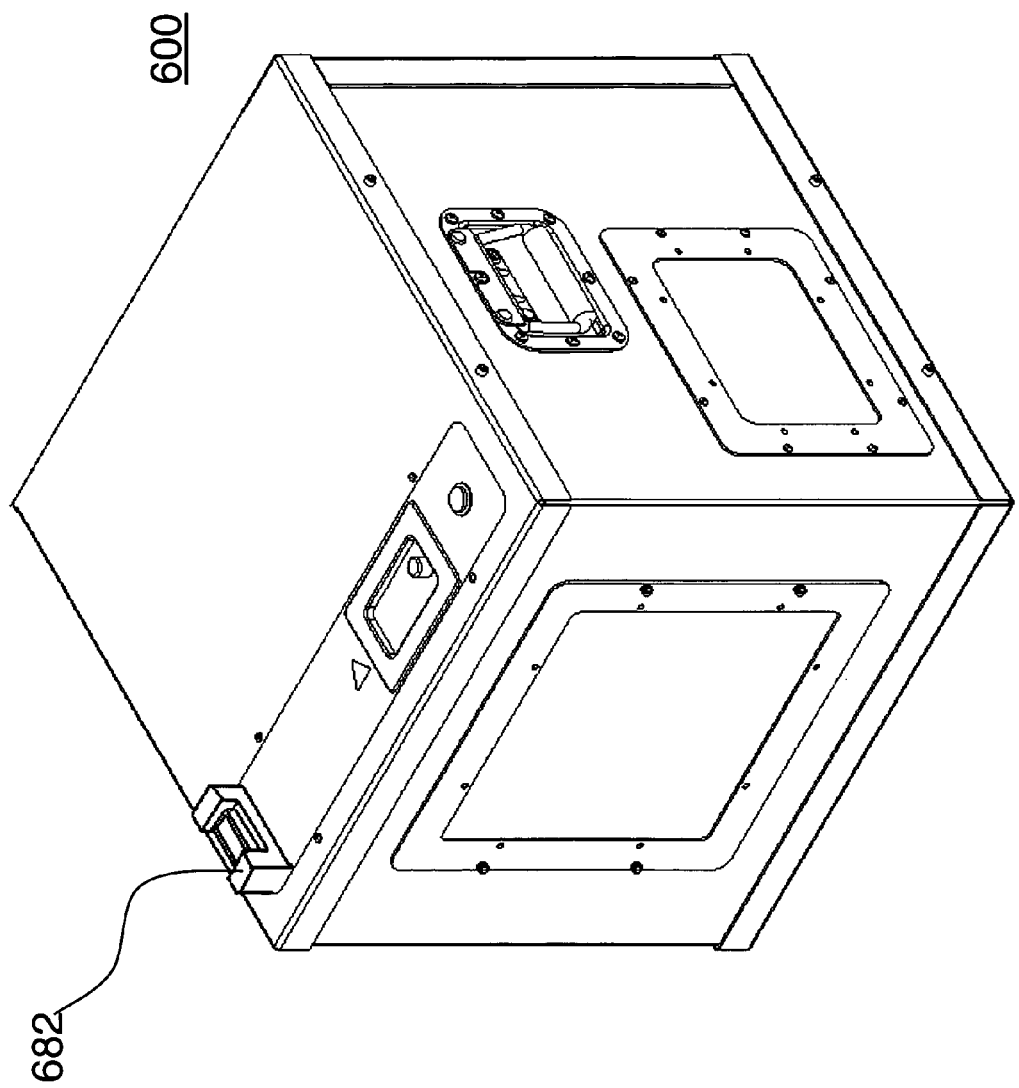
FIG. 6 is a perspective view of an analytical instrument with a cartridge installed in accordance with one embodiment.

In one implementation, the apparatus has three main components: a sample cartridge 100, a sampler 300, and an analytical instrument 600. In operation, a sample cartridge 100 is inserted into the sampler 300 by a user. The user then activates the sampler 300 to trap desired analytes in the cartridge 100. The cartridge 100 is then later removed from the sampler 300 and coupled to an analytical instrument 600 for analysis. One implementation of a sample cartridge 100 is depicted in FIGS. 1A-1C. Another implementation of a sample cartridge 200 is depicted in FIGS. 2A-2B. One implementation of a sampler 300 is depicted in FIGS. 3A-3G. A second implementation of a sampler 400 is depicted in FIGS. 4A-4D. A third implementation of a sampler 500 is depicted in FIGS. 5A-5B. An analytical instrument 600 is depicted in FIG. 6.

A sample cartridge 100 is a device used to trap analytes. When air is pulled/pushed through the cartridge 100 chemical analytes will be stored in the cartridge 100 for later analysis by an analytical instrument 600. In one implementation, the sample cartridge 100 may include sorbent tubes (114 in FIG. 1C) or a Tedlar bag (not shown) to trap analytes. Alternatively, the sample cartridge 100 may comprise disc filters, SPME fibers, evacuated cylinders, and/or any other trap that is known in the art. In addition, different cartridges 100 may be used for different target missions. For example, one cartridge 100 may be used for volatile chemicals, while another cartridge 100 may be for biological agents. This implementation is only exemplary and other methods of trapping analytes in the sample cartridge 100 may be used.

In one implementation, as shown in FIG. 1C, the cartridge 100 has separate inlet 102 and outlet 104 ports, both of which automatically seal the cartridge closed when it is not connected to a sampler 300 or an analytical instrument 600. This design prevents the sample from being contaminated by any other sources and also protects the operator from exposure to the sample. In one implementation, the self-sealing feature can be accomplished using spring force or magnetic force, though any method of self-sealing the inlet 102 or outlet 104 ports may be used.

An embodiment utilizing spring force for self-sealing is illustrated in FIG. 1C. A spring 108 mounted in a cartridge 100 maintains a bearing or valve ball 110 in a normally closed position against seat 112. When a cartridge 100 is inserted, force applied to the bearing or valve ball 110 causes the spring 108 to compress. With the spring 108 compressed, bearing or valve ball 110 separates from seat 112, allowing the transfer of a sample or other material into and/or out of cartridge 100 via inlet 102 and outlet 104 ports.

The use of a self-sealing removable cartridge makes decontamination of the handheld sampler 300 easier. Because the cartridge 100 can be removed from the sampler 300, the external surfaces and the entire flow path of the sampler 300 may be decontaminated without fear of harming the sample. Moreover, the self-sealing nature of the tubes allows the external surfaces of the cartridges 100 to be decontaminated separately before moving the cartridge 100 into a safe zone for analysis.

In another implementation, the cartridge 100 may also include memory for storing data relating to the sample, as shown in FIG. 1A. This data includes any information pertaining to the sample including global positioning system ("GPS") location when sampled, volume of sample collected, date/time stamp, voice data, image data, or any other information to be stored by the user. By storing such information, the devices removes the need for an operator to separately record the information. The illustration in FIG. 1A shows a memory chip 6 used as memory; however, any suitable memory may be used, including RAM, ROM, flash drive, or memory card. The embodiment of FIG. 1A illustrates an electronic interface 116 that may be used to transfer stored information between the cartridge 100 and a sampler or a personal computer ("PC").

Another embodiment of a cartridge 200 is shown in FIG. 2A and in cross-section in 2B. Cartridge 200 may include the same or similar features as cartridge 100, and consistent numbering is used wherever possible. For example, cartridge 200 may include an inlet 202 and outlet 204 connected to a sorbent tube 214. The inlet 202 and 204 may automatically seal the cartridge 200 closed when it is not connected to a sampler 300, 400 or an analytical instrument 600. As illustrated in FIG. 2B, cartridge 200 may use spring force for self-sealing. A spring 208 mounted in a cartridge 200 maintains a bearing or valve ball 210 in a normally closed position against valve seat 212. When the cartridge 200 is inserted into a sampler 300, 400, the spring 208 is compressed; thereby opening inlet 202 and/or outlet 204. This embodiment also illustrates an electronic interface 216 that may be used to transfer information between the cartridge 200 and a sampler or a PC. The cartridge 200 may further include a heater 217 and a thermocouple 219 configured to heat and measure the temperature of analytes within the tube 214. Additionally, the cartridge 200 may include a clip 205 configured to secure the cartridge within a sampler, PC, or other desired device.

A sampler may be used in conjunction with the cartridge to obtain a sample for eventual analysis. In one implementation, the sampler is a small, lightweight, battery 46 operated device that can easily be transported to an area of possible contamination. FIGS. 3A-3G illustrate one embodiment of such a sampler 300 having a "pistol" shape. FIGS. 4A-4D illustrate another embodiment of such a sampler 400 having shape similar to a personal digital assistant ("PDA"). FIGS. 5A-5B illustrate yet another embodiment of a sampler 500. Samplers 300, 400, and 500 may include the same or similar features, and consistent numbering is used wherever possible.

Figure 3A:
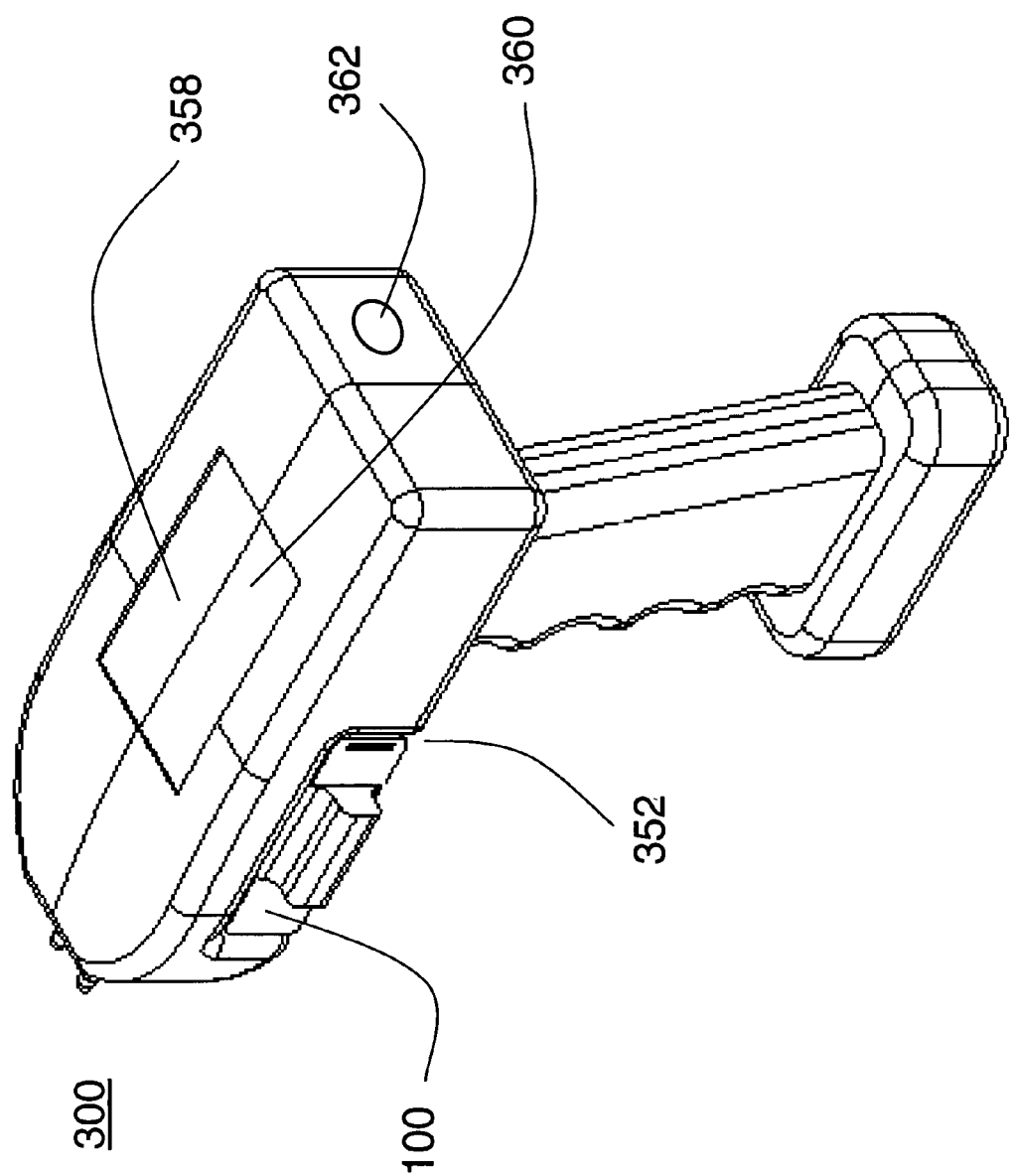
FIG. 3A is a perspective view of a handheld sampler with a cartridge installed in accordance with one embodiment.
Figure 3B:
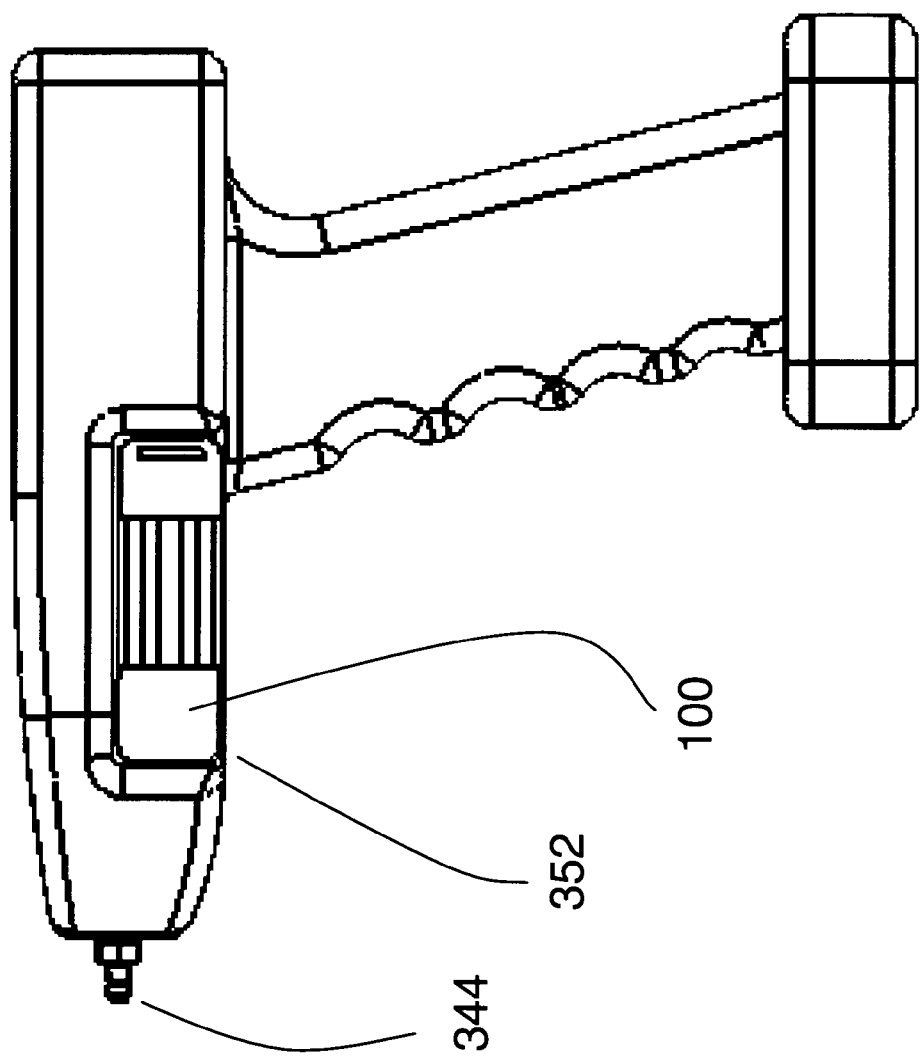
FIG. 3B is a side view of a handheld sampler with a cartridge installed in accordance with one embodiment.
Figure 3C:
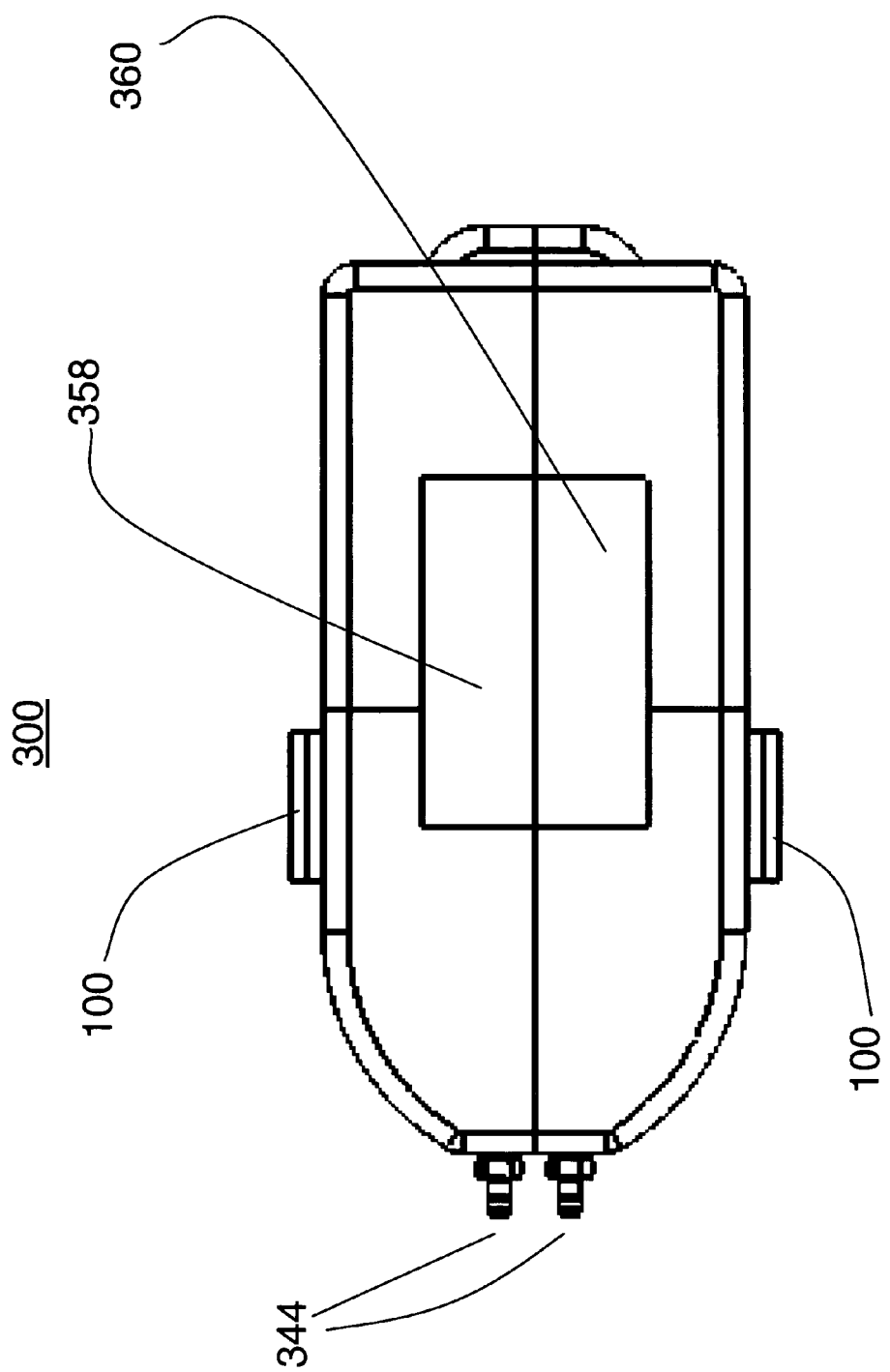
FIG. 3C is a top view of a handheld sampler with a cartridge installed in accordance with one embodiment.
Figure 3D:
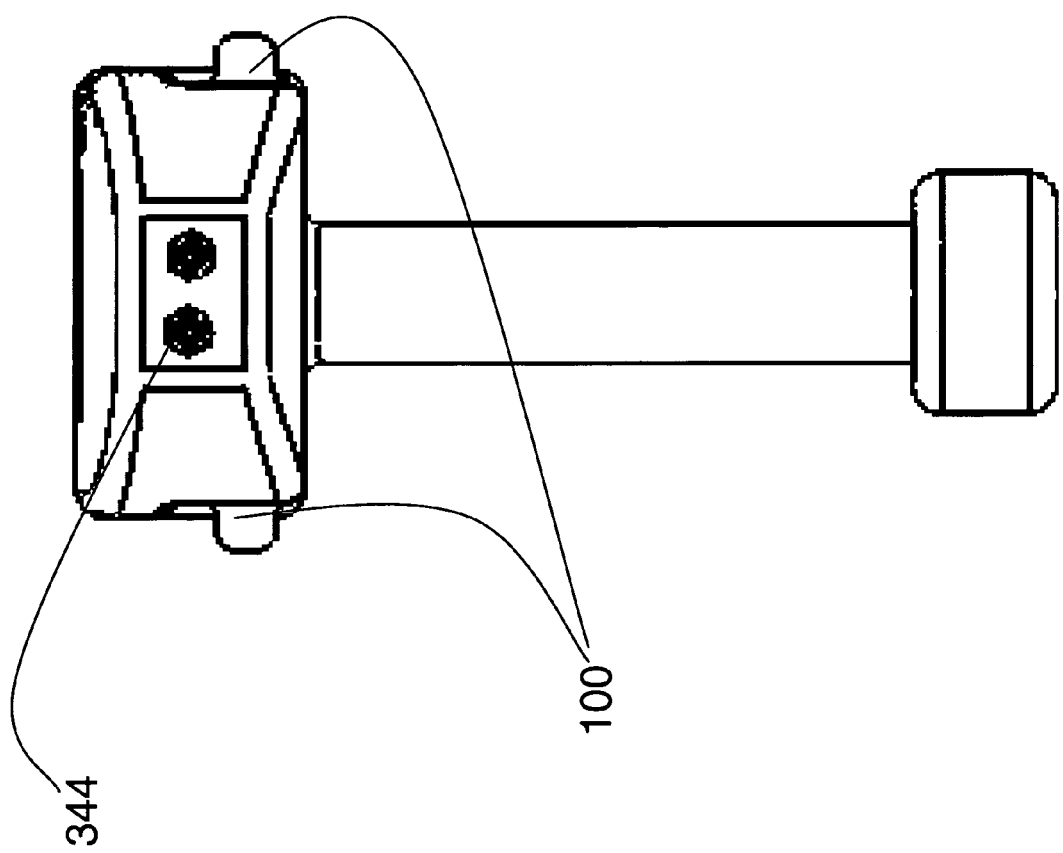
FIG. 3D is a front view of a handheld sampler with a cartridge installed in accordance with one embodiment.
Figure 3E:
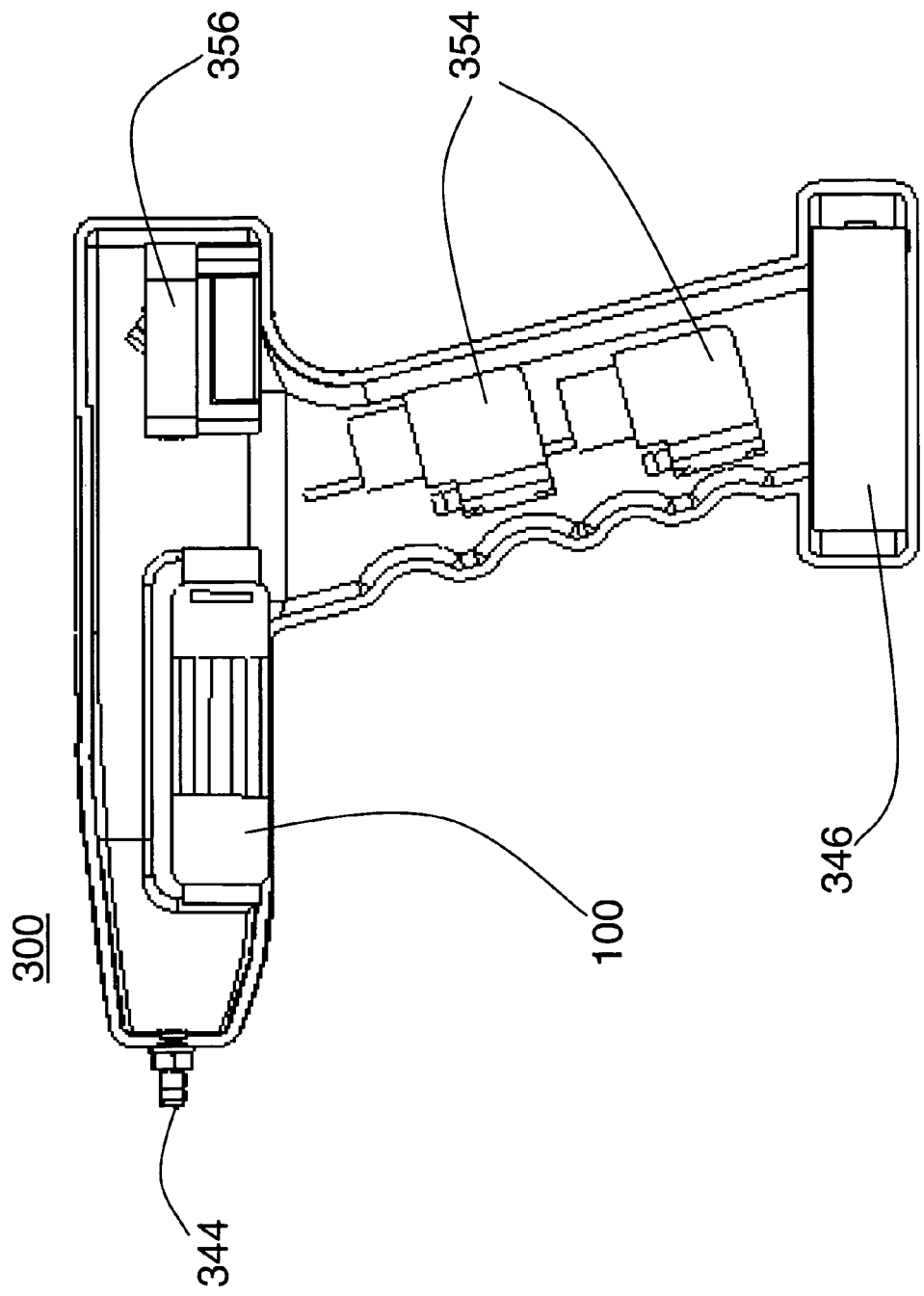
FIG. 3E is an interior side view of a handheld sampler with a cartridge installed in accordance with one embodiment.
Figure 3F:
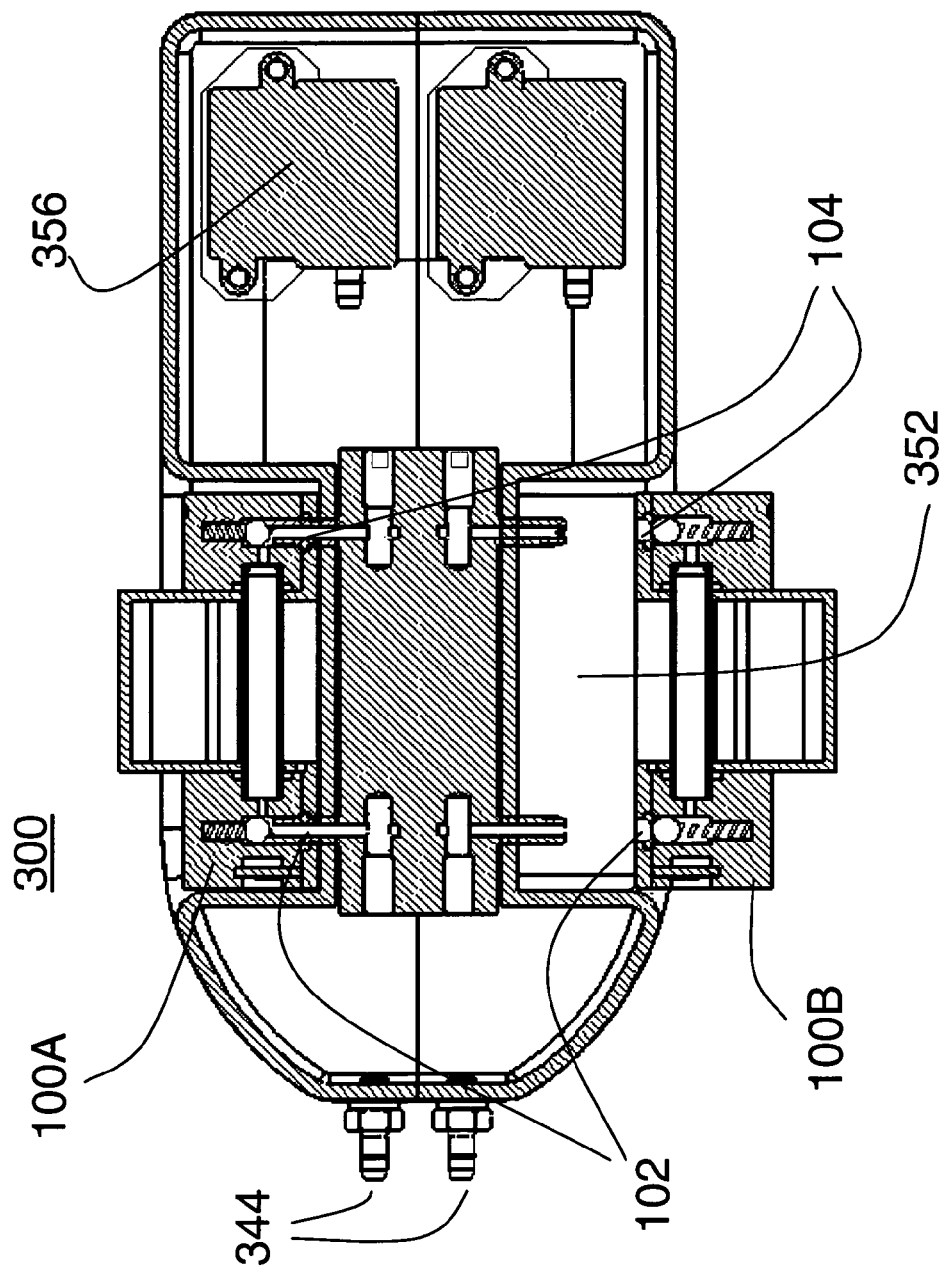
FIG. 3F is a second interior top view of a handheld sampler with a cartridge installed in accordance with one embodiment.
Figure 3G:
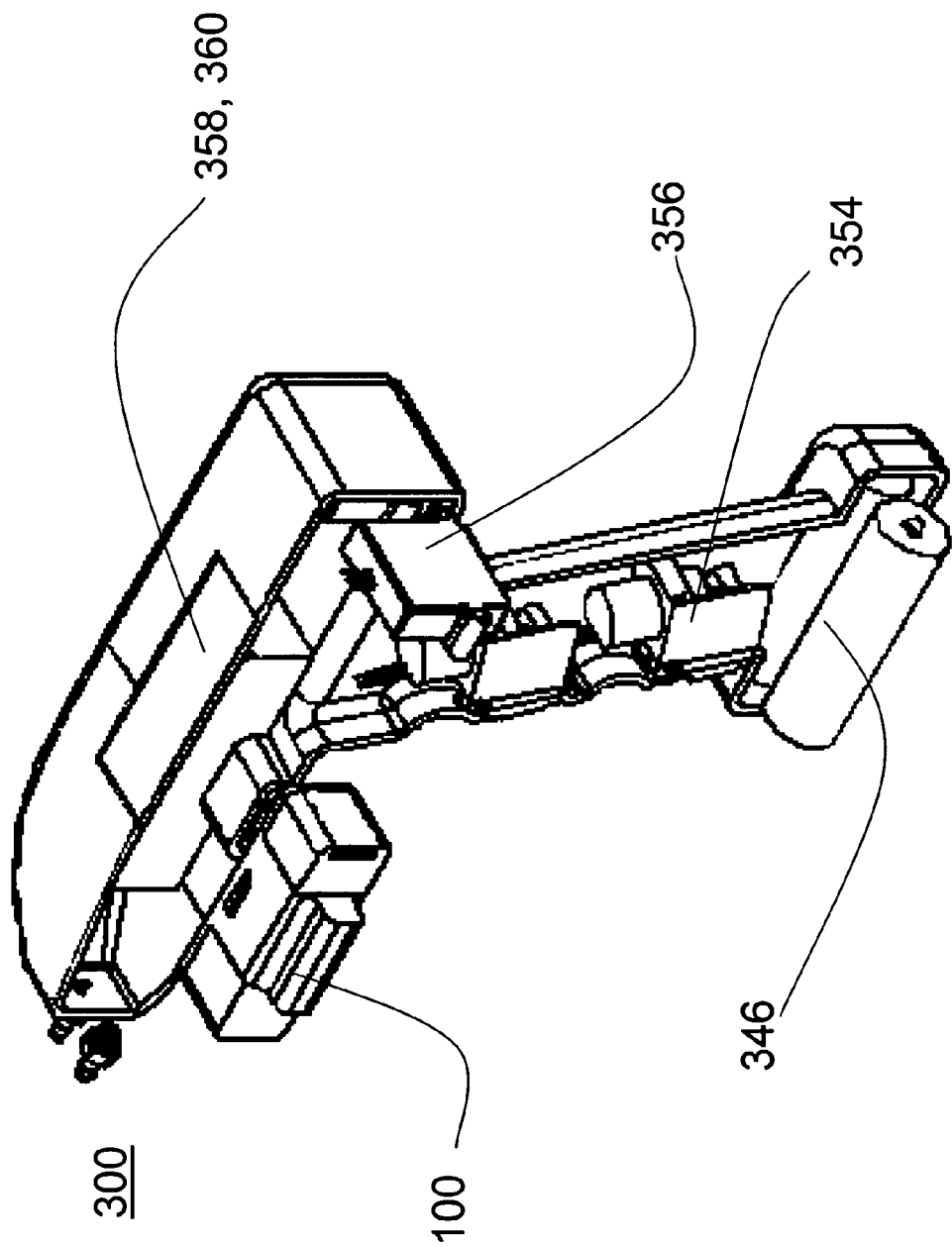
FIG. 3G is a perspective cut-away view of a handheld sampler with a cartridge installed in accordance with one embodiment.

The sampler 300 may include a docking port 352 to accept the sampling cartridge 100, as shown in FIGS. 3A and 3F. In a similar fashion, cartridge 100 may insert into sampler 400 (as shown in FIGS. 4B-4C) and cartridge 200 may insert into sampler 500 (as shown in FIG. 5A). The docking port 352 will open the sealed fluidic ports of the cartridge 100 and will connect with the electronic interface 116 of the sample cartridge. FIG. 2G illustrates two cartridges 100A and 100B in different states of insertion. Cartridge 100A is fully inserted into the sampler 300, thereby opening the inlet 102 and outlet 104 ports of the cartridge 100A. Cartridge 100B is substantially removed from the sampling dock 352, leaving inlet 102 and outlet 104 ports closed.

Figure 7:
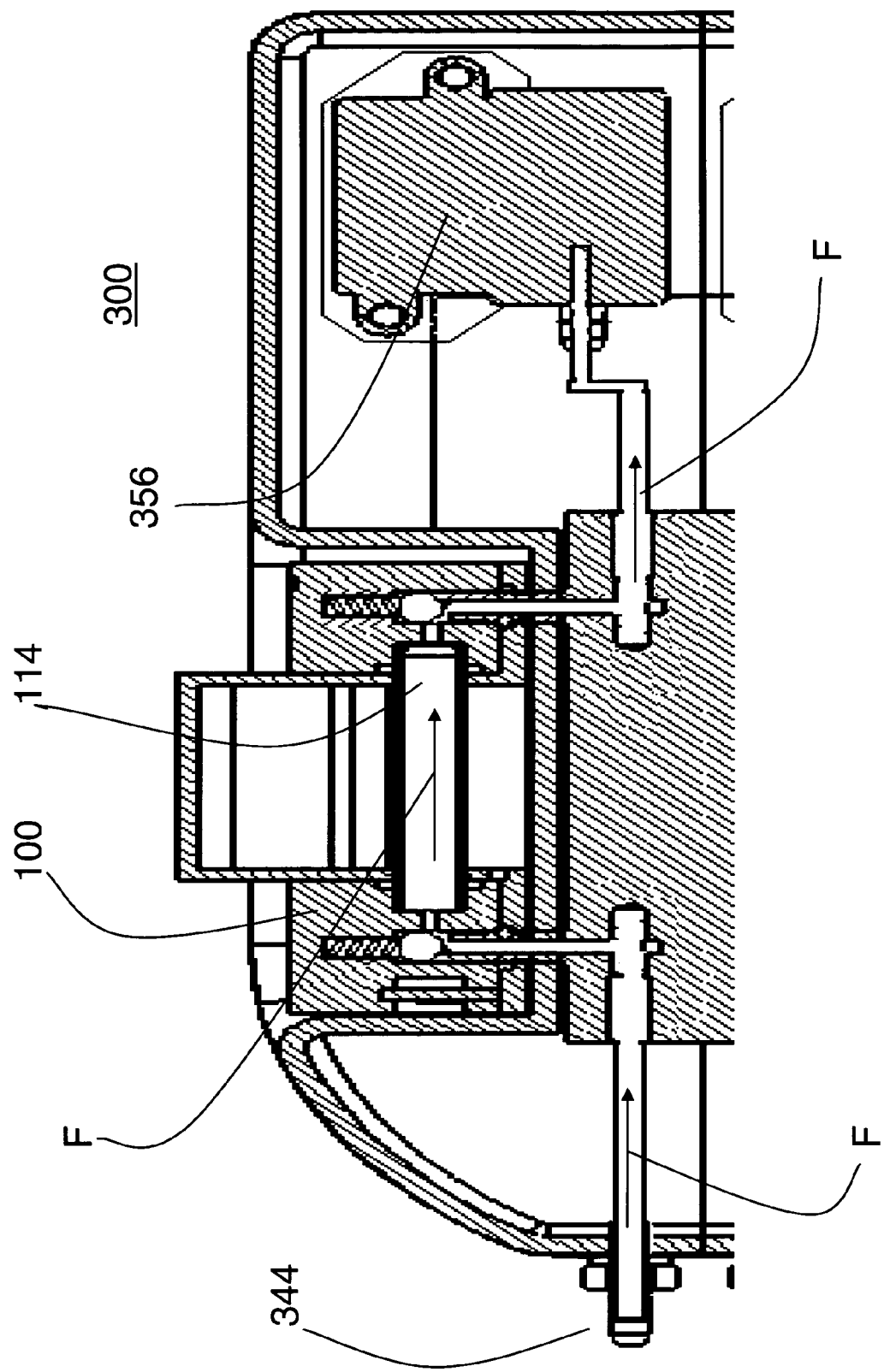
FIG. 7 is partial interior top view of a handheld sampler with a cartridge installed in accordance with one embodiment, illustrating the flow of a sample.
Figure 8:
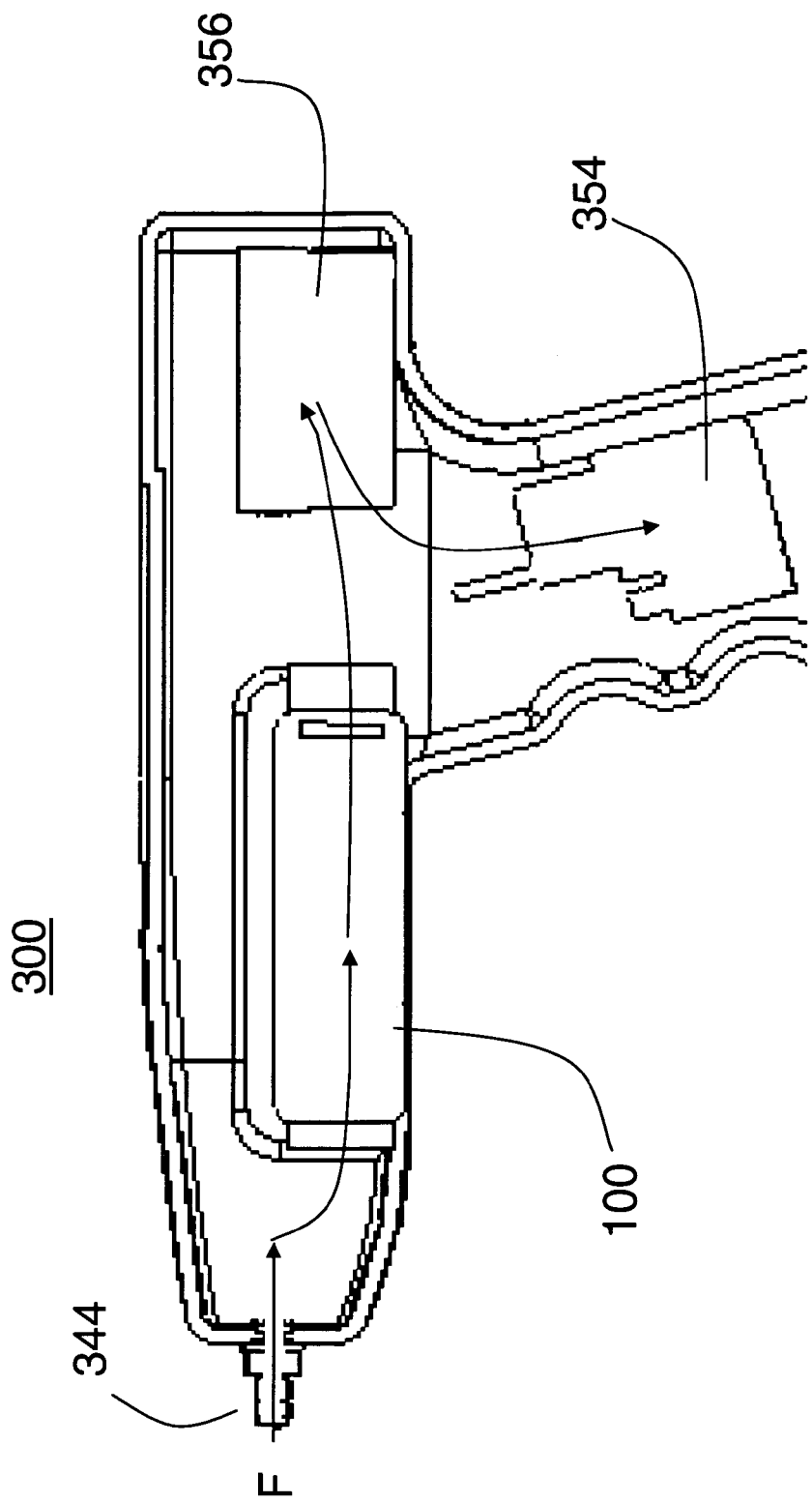
FIG. 8 is a side view of a handheld sampler with a cartridge installed in accordance with one embodiment, illustrating the flow of a sample.

As shown in FIG. 3E, in one implementation, the sampler 300 will include a sample pump 354 to pull air through the cartridge 100 via a sampler inlet 344 and will include a flow/volume sensor 356 to measure the sample volume. The sampler 300 may have one or multiple sample flow paths F to allow for sampling of sequential or simultaneous sampling of multiple cartridges 100, as shown in FIGS. 7 and 8. In one implementation, the sampler may include a filter (not shown) disposed at a point upstream of sample cartridge 100 to filter debris and other solid or liquid particulates as desired. Such filters are also well-known in the art. In one aspect, the sample pump 354 may be adapted to draw in volumes of matter in other than a gaseous state. The intake system may be adapted to draw in, for example, gasses bearing solid or liquid particulates, liquids, or colloidal suspensions.

In one implementation, the sampler 300 may include a CPU, display 358, and/or keypad 360, as shown in FIG. 3A. The keypad 360 may be used to select an operation mode or to enter data about the sample or sample cartridge 100. Once a particular operation mode is selected, the CPU will cause the sampler 300 to run in the selected operation mode. Different operation modes may be selected that operate the apparatus according to varying parameters. For example, an operation mode may be selected that operates the sample pump 354 for a predetermined length of time. Another operation mode may be selected that operates the sample pump 354 until a predetermined volume of gas has passed through the flow meter. Various operation modes may be programmed into the memory by a user, as unique operation modes are developed. Alternatively, the apparatus may be operated manually. The display 358 may be used to display information related to operation of the sampler 300 as well as other information about the sample, sample cartridge 100, or the environment. In one implementation in which the cartridge 100 includes memory 106 for storing data, the sampler 300 will record critical information pertinent to the sample collected including GPS location when sampled, volume of sample collected, date/time stamp, voice data, and image data to the sampling cartridge 100 for use when it is later analyzed.

In one implementation, the sampler 300 will also include an interface 362 (FIG. 3A) to connect the sampler 300 to an analytical instrument 600 or a PC. This connection will allow for programming a smart sampler 300. Multiple programmable options will be available to collect samples based on time, volume, or manual control by an operator.

In yet another implementation, the sampler 300 will be outfitted with a chemical trigger technology to let the user know when it is likely that a chemical of interest exists in the environment and should be sampled. In one implementation, the sampler 300 may include a FAIMS (high-Field Asymmetric waveform Ion Mobility Spectrometry) detector, a Photo Ionization Detector, or a Metal Oxide Detector, to detect the presence of chemicals in the atmosphere in order to alert the user to obtain a sample. These implementations are merely exemplary and other triggers may be used.

Additional sampler embodiments 400, illustrated in FIGS. 4A-4D, may operate similarly to the embodiments illustrated in FIGS. 3A-3G, and may include similar components. For example, sampler 400 may include a pump 454, flow/volume sensor 456, inlet port 444, display 458, and keyboard 460.

Further sampler embodiments 500, illustrated in FIGS. 5A-5B, may also operate similarly to the embodiments illustrated in FIGS. 3A-3G. Sampler 500 may include a display 558, keyboard 560, inlet ports 544, a pump 554, and a flow/volume sensor 556. Sampler 500 may accept cartridge 200 as previously described.

FIG. 6 depicts an analytical instrument 600. The analytical instrument 600 is used to perform a chemical analysis on the analytes in the sample cartridge 100, 200. The analytical instrument 600 may be any instrument for performing chemical analysis such as a mass spectrometer (MS) or a flame ionization detector (FID). Alternatively, the analytical instrument 600 may be a chemical separation device, such as, e.g., a gas-chromatograph (GC). The analytical instrument 600 may also be a combination GC/MS, GC/electron capture detector (ECD), or GC/FID.

In one implementation, the analytical instrument 600 will have a docking port 682 to mate with the sample cartridge 100, 200. This port will open the sealed fluidic ports of the cartridge 100, 200 and will connect with the electronic interface 116, 216 of the sample cartridge 100, 200. In one implementation in which the cartridge 100, 200 includes memory 106, 206 for storing data, when the cartridge 100, 200 is attached to the instrument it will access any data stored on the cartridge's 100, 200 memory chip 106, 206. This data will be downloaded to the instrument when the cartridge 100, 200 is analyzed. This data can be used to complete a quantification analysis and will provide a direct line chain of evidence for important information documented at the point of sample collection. In one implementation, the instrument may also include a cartridge (not shown) that can be used as an external standard to calibrate the sample.

Other embodiments will be apparent to those skilled in the art from consideration of the specification and practice of the disclosure herein. It is intended that the specification and examples be considered as exemplary only, with a true scope and spirit of the disclosure being indicated by the following claims.

What is claimed is:

1. A sample cartridge for storing an atmospheric sample, the sample cartridge comprising:
   a self-sealing inlet port configured to removeably couple to a first apparatus, and automatically close when the inlet port is not in use;
   a self-sealing outlet port configured to removeably couple to second apparatus, and automatically close when the outlet port is not in use; and
   a sample retention portion in fluid communication with and disposed between the inlet port and outlet port and adapted to trap an atmospheric sample.

2. The sample cartridge of claim 1, wherein the self-sealing inlet port and the self-sealing outlet port are spring actuated.

3. The sample cartridge of claim 2, further comprising:
   a first spring and a first ball bearing operably arranged within the inlet port, the inlet port having a first seat;
   a second spring and a second ball bearing operably arranged within the outlet port, the outlet port having a second seat;
   wherein the first spring is configured to seal the first ball bearing within the inlet port on the first seat, thereby keeping the inlet port closed when the inlet port is not in use; and
   wherein the second spring is configured to seal the second ball bearing within the outlet port on the second seat, thereby keeping the outlet port closed when the outlet port is not in use.

4. The sample cartridge of claim 1, wherein the self-sealing inlet port and the self-sealing outlet port are magnetically actuated.

5. The sample cartridge of claim 1, further comprising a memory device configured to store data.

6. The sample cartridge of claim 5, wherein the memory device is configured to store at least one parameter identifying a sample.

7. The sample cartridge of claim 6, wherein the at least one parameter is selected from the group consisting of GPS location when a sample is collected, volume of a sample collected, the time a sample was collected, and the date a sample was collected.

8. The sample cartridge of claim 5, wherein the memory device is further configured to store voice data.

9. The sample cartridge of claim 5, wherein the memory device is further configured to store image data.

10. The sample cartridge of claim 1, wherein the sample retention portion comprises a sorbent tube.

11. The sample cartridge of claim 1 wherein the first and second apparatus are the same apparatus.

12. The sample cartridge of claim 1 wherein the first apparatus is a sampling apparatus.

13. The sample cartridge of claim 1 wherein the second apparatus is an analytical apparatus.

14. An air sampling cartridge for use with a sampling apparatus, the cartridge comprising:
   a housing;
   at least one sample storage assembly, at least a portion of the assembly being in fluid communication with a coupling assembly associated with one exterior portion of the housing and configured to couple with the sampling apparatus; and
   at least one memory device, the memory device being in electrical communication with a communication interface associated with another exterior portion of the housing and configured to couple with the sampling apparatus.

15. The cartridge of claim 14 wherein in one cross section, the housing substantially defines a rectangle having a length extending to and greater than its ends-width; and the coupling assembly being associated with one of the ends of the housing.

16. The cartridge of claim 14 wherein in one cross section, the housing substantially defines a rectangle having a length extending to and greater than its ends-width; and the communication interface is associated with one of the ends of the housing.

17. The cartridge of claim 14 wherein in one cross section, the housing substantially defines a rectangle having a length extending to and greater than its ends-width; at least one end defining a locking assembly configured to engage the sampling apparatus and lock the cartridge to the sampling apparatus.

18. The cartridge of claim 17 wherein the locking assembly is configured as a clip.

19. The cartridge of claim 14 further comprising a heating element operatively engaged with the sample storage assembly, the heating element being in electrical communication with an electrical interface associated with an exterior portion of the housing.

20. The cartridge of claim 19 further comprising a thermocouple in electrical communication with the electrical interface.

21. The cartridge of claim 20 wherein the memory device is in electrical communication with the thermocouple.

22. The cartridge of claim 21 wherein the sample storage assembly can be heated and/or cooled without damaging the memory device.

23. The cartridge of claim 14 wherein the memory device includes data associating itself with an identifier on the exterior of the housing.

24. The cartridge of claim 14 wherein the memory device is configured to retain data associated with the time, date, and/or place of sample acquisition.

* * * * *

UNITED STATES PATENT AND TRADEMARK OFFICE
CERTIFICATE OF CORRECTION

PATENT NO. : 8,146,448 B2  Page 1 of 1
APPLICATION NO. : 12/216027
DATED : April 3, 2012
INVENTOR(S) : Matthew Briscoe, Brent Rardin and Dennis Barket, Jr.

It is certified that error appears in the above-identified patent and that said Letters Patent is hereby corrected as shown below:

Column 2, line 28 – Replace "inlet 202 and 204" with -- inlet 202 and outlet 204--

Signed and Sealed this
Fourteenth Day of August, 2012

David J. Kappos
*Director of the United States Patent and Trademark Office*